(12) United States Patent
Tran et al.

(10) Patent No.: US 10,893,938 B2
(45) Date of Patent: Jan. 19, 2021

(54) STENTED PROSTHESIS DELIVERY SYSTEM HAVING A BUMPER

(71) Applicant: Medtronic Vascular, Inc., Santa Rosa, CA (US)

(72) Inventors: Don Tran, Novato, CA (US); Martha Barajas-Torres, Santa Rosa, CA (US); Marian Lally, Ballybrit (IE); Michael Gloss, Minneapolis, MN (US); Timothy Groen, Rush City, MN (US); Leonel Mendoza, Santa Rosa, CA (US); Siyan Som, Fulton, CA (US); Michele Silver, Healdsburg, CA (US); Nathan Brown, Santa Rosa, CA (US); Jill Mendelson, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 126 days.

(21) Appl. No.: 15/449,471

(22) Filed: Mar. 3, 2017

(65) Prior Publication Data

US 2017/0252161 A1 Sep. 7, 2017

Related U.S. Application Data

(60) Provisional application No. 62/303,274, filed on Mar. 3, 2016.

(51) Int. Cl.
*A61F 2/24* (2006.01)
*A61F 2/966* (2013.01)

(52) U.S. Cl.
CPC .......... *A61F 2/2436* (2013.01); *A61F 2/2418* (2013.01); *A61F 2/966* (2013.01);
(Continued)

(58) Field of Classification Search
CPC ...... A61F 2/2436; A61F 2/2418; A61F 2/966; A61F 2/95; A61F 2/954; A61F 2/962
(Continued)

(56) References Cited

U.S. PATENT DOCUMENTS 5,035,706 A 7/1991 Giantureo et al.
5,693,084 A 12/1997 Chuter
(Continued)

FOREIGN PATENT DOCUMENTS

WO WO2009/091509 7/2009

OTHER PUBLICATIONS

PCT/US2017/020738, The International Search Report and the Written Opinion of the International Searching Authority, dated Apr. 24, 2017.
(Continued)

*Primary Examiner* — George J Ulsh
*Assistant Examiner* — Andrew P. Restaino
(74) *Attorney, Agent, or Firm* — Dicke, Billig & Czaja, PLLC

(57) ABSTRACT

Numerous delivery devices for delivery of a stented prosthesis, such as a stented prosthetic heart valve. Various delivery devices include a capsule that is advanced proximally to retain the stented prosthesis, which is secured over an inner shaft assembly of the delivery device. The delivery device further includes a bumper or bumper assembly to provide a smooth transition of the capsule over the stented prosthesis. In some alternate disclosed embodiments, the bumper further serves to connect various elements of the inner shaft assembly. Additional embodiments include a bumper assembly arranged and configured to longitudinally expand and contract to substantially fill any open space as the capsule is retracted from the stented prosthesis, which prevents kinking in the capsule. Additional embodiments
(Continued)

include proximal and/or distal bumpers for temporarily covering and smoothing the ends of the stented prosthesis as part of a delivery device that does not include a capsule.

7 Claims, 9 Drawing Sheets

(52) U.S. Cl.
CPC .......... *A61F 2002/9665* (2013.01); *A61F 2230/0067* (2013.01); *A61F 2250/0039* (2013.01)

(58) Field of Classification Search
USPC ........................................................ 623/2.11
See application file for complete search history.

(56) References Cited

U.S. PATENT DOCUMENTS

| | | | |
|---|---|---|---|
| 5,776,186 A | 7/1998 | Uflacker | |
| 6,113,608 A | 9/2000 | Monroe et al. | |
| 6,280,465 B1 | 8/2001 | Cryer | |
| 6,517,550 B1 | 2/2003 | Konya et al. | |
| 6,733,521 B2 | 5/2004 | Chobotov et al. | |
| 6,740,111 B1 | 5/2004 | Lauterjung | |
| 7,033,390 B2 | 4/2006 | Johnson et al. | |
| 7,329,275 B2 | 2/2008 | Yee | |
| 7,503,929 B2 | 3/2009 | Johnson et al. | |
| 7,758,625 B2* | 7/2010 | Wu | A61F 2/95 623/1.11 |
| 7,935,140 B2* | 5/2011 | Griffin | A61F 2/95 623/1.11 |
| 8,403,981 B2 | 3/2013 | Forster et al. | |
| 8,518,098 B2* | 8/2013 | Roeder | A61F 2/95 623/1.11 |
| 9,198,783 B2* | 12/2015 | Douk | A61F 2/86 |
| 9,592,142 B2* | 3/2017 | Dillon | A61F 2/966 |
| 2003/0114910 A1* | 6/2003 | Juhani Laakso | A61F 2/95 623/1.11 |
| 2005/0119722 A1 | 6/2005 | Styrc et al. | |
| 2006/0074477 A1* | 4/2006 | Berthiaume | A61F 2/95 623/1.11 |
| 2006/0100687 A1* | 5/2006 | Fahey | A61F 2/95 623/1.11 |
| 2009/0281610 A1 | 11/2009 | Parker | |
| 2009/0318947 A1* | 12/2009 | Garcia | A61B 17/12022 606/191 |
| 2010/0168835 A1* | 7/2010 | Dorn | A61F 2/95 623/1.11 |
| 2010/0286768 A1 | 11/2010 | Alkhatib | |
| 2011/0040366 A1 | 2/2011 | Goetz et al. | |
| 2012/0277734 A1 | 11/2012 | Goetz et al. | |
| 2013/0013047 A1* | 1/2013 | Ramos | A61F 2/966 623/1.11 |
| 2013/0110223 A1* | 5/2013 | Munsinger | A61F 2/966 623/1.11 |
| 2013/0245752 A1 | 9/2013 | Goetz et al. | |
| 2013/0304179 A1* | 11/2013 | Bialas | A61F 2/966 623/1.11 |
| 2013/0338755 A1 | 12/2013 | Goetz et al. | |
| 2014/0296959 A1* | 10/2014 | Leanna | A61F 2/95 623/1.11 |
| 2014/0330368 A1 | 11/2014 | Gloss et al. | |
| 2015/0112430 A1 | 4/2015 | Creaven et al. | |
| 2015/0238315 A1 | 8/2015 | Rabito et al. | |
| 2015/0297379 A1* | 10/2015 | Green | A61F 2/95 623/1.12 |
| 2016/0270935 A1* | 9/2016 | Rasmussen | A61F 2/07 |
| 2017/0165067 A1* | 6/2017 | Barajas-Torres | A61F 2/2415 |

OTHER PUBLICATIONS

U.S. Appl. No. 62/117,013, filed Feb. 17, 2015, Duffy.

* cited by examiner

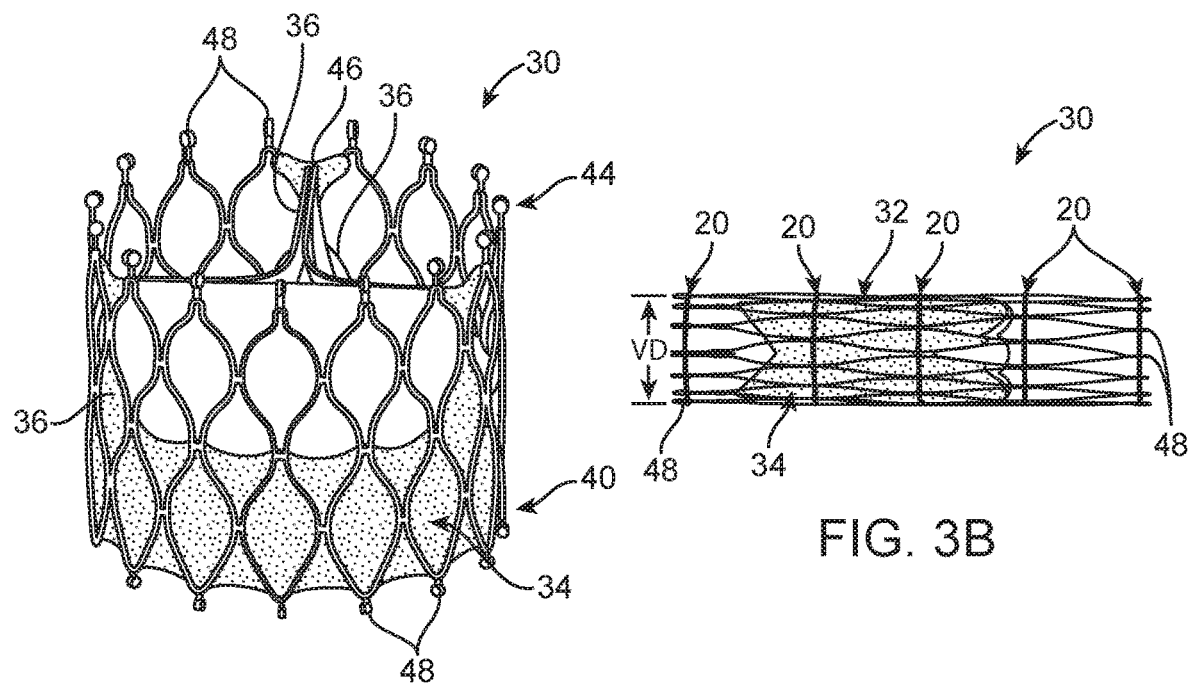
FIG. 3A
FIG. 3B
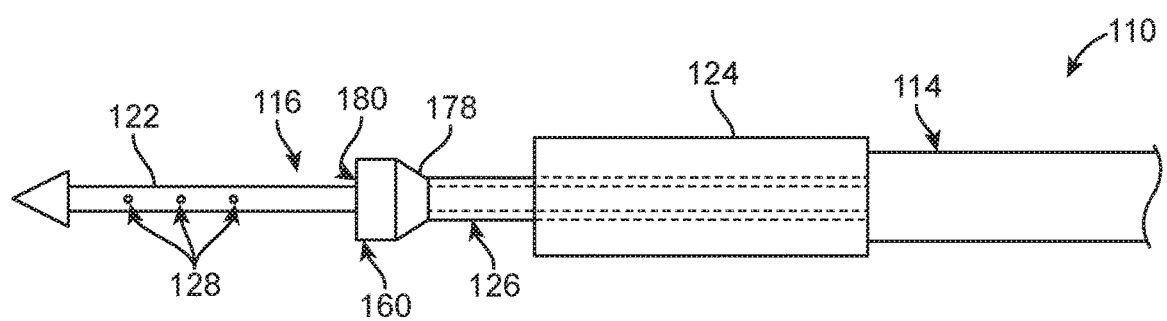
FIG. 4A
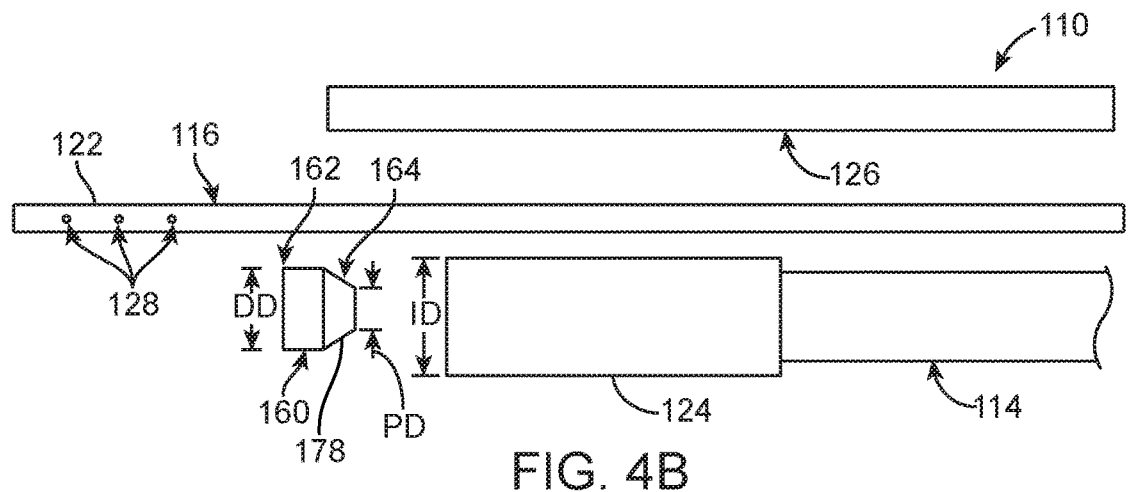
FIG. 4B

STENTED PROSTHESIS DELIVERY SYSTEM HAVING A BUMPER

CROSS-REFERENCE TO RELATED APPLICATIONS

This Non-Provisional Patent Application claims the benefit of the filing date of U.S. Provisional Patent Application Ser. No. 62/303,274, filed Mar. 3, 2016, entitled "STENTED PROSTHETIC HEART VALVE DELIVERY SYSTEM HAVING A BUMPER," the entire teachings of which are incorporated herein by reference.

BACKGROUND

The disclosure relates to delivery devices for stented prosthesis (e.g., stented prosthetic heart valve) loading and implantation. More particularly, the present disclosure provides for delivery devices that prevent a proximal end of the stented prosthesis from catching or snagging on the delivery device or causing injury to the patient.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The present disclosure presents improvements directed to the related art.

SUMMARY

The present disclosure relates to numerous delivery devices and methods for stented prosthesis or stented prosthetic heart valve (hereinafter "prosthetic valve") loading and implantation. Various delivery devices can include an outer sheath assembly, an inner shaft assembly and a handle assembly. The delivery device provides a loaded delivery arrangement in which the prosthetic valve is loaded and compressed over the inner shaft assembly. Compressive tension of the prosthetic valve can be varied and adjusted with one or more elongate tension members actuated by the handle assembly. In this way, the delivery device can be manipulated to permit the prosthetic valve to self-expand and partially release from the inner shaft assembly.

When compressed, most stented prosthesis and stented prosthetic heart valve designs have a rough outer surface, which can cause damage to the patient during delivery to a native heart valve or other target site. Therefore, various embodiments disclosed herein include a delivery device having a protective sheath or capsule covering the outer surface of the prosthetic valve until the prosthetic valve is in position and ready to be deployed. Capsules, however, can snag on a proximal end of the prosthetic valve when the capsule is advanced over the prosthetic valve during loading or recapture of the prosthetic valve within the capsule. In various disclosed embodiments, the delivery device includes a bumper to provide a smooth transition of the capsule over the prosthetic valve. In some alternate disclosed embodiments, the bumper further serves to connect various elements of the inner shaft assembly.

Further disclosed embodiments include a bumper assembly having at least one bumper and a biasing member positioned within the capsule of the delivery device. The bumper assembly is arranged and configured to longitudinally expand and contract to substantially fill any open space as the capsule is retracted from the prosthetic valve, which prevents kinking in the capsule.

Other disclosed embodiments are designed for use with a delivery device that does not include a capsule. These embodiments include a proximal and an optional distal bumper that each smooth respective edges of the prosthetic valve during delivery.

Methods of loading the stented prosthesis to the disclosed delivery devices are also disclosed.

BRIEF DESCRIPTION OF THE DRAWINGS

FIG. 3A is a perspective view of a stented prosthetic heart valve that can be used with the delivery devices disclosed herein shown in an expanded arrangement.

FIG. 3B is a front view of the stented prosthetic heart valve of FIG. 3A in a compressed arrangement.

FIG. 4A is a partial, schematic illustration of a delivery device for delivering the stented prosthetic heart valve of FIGS. 3A-3B having a bumper and a capsule for sheathing the stented prosthetic heart valve.

FIG. 4B is a partial, exploded schematic illustration of the delivery device of FIG. 4A.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
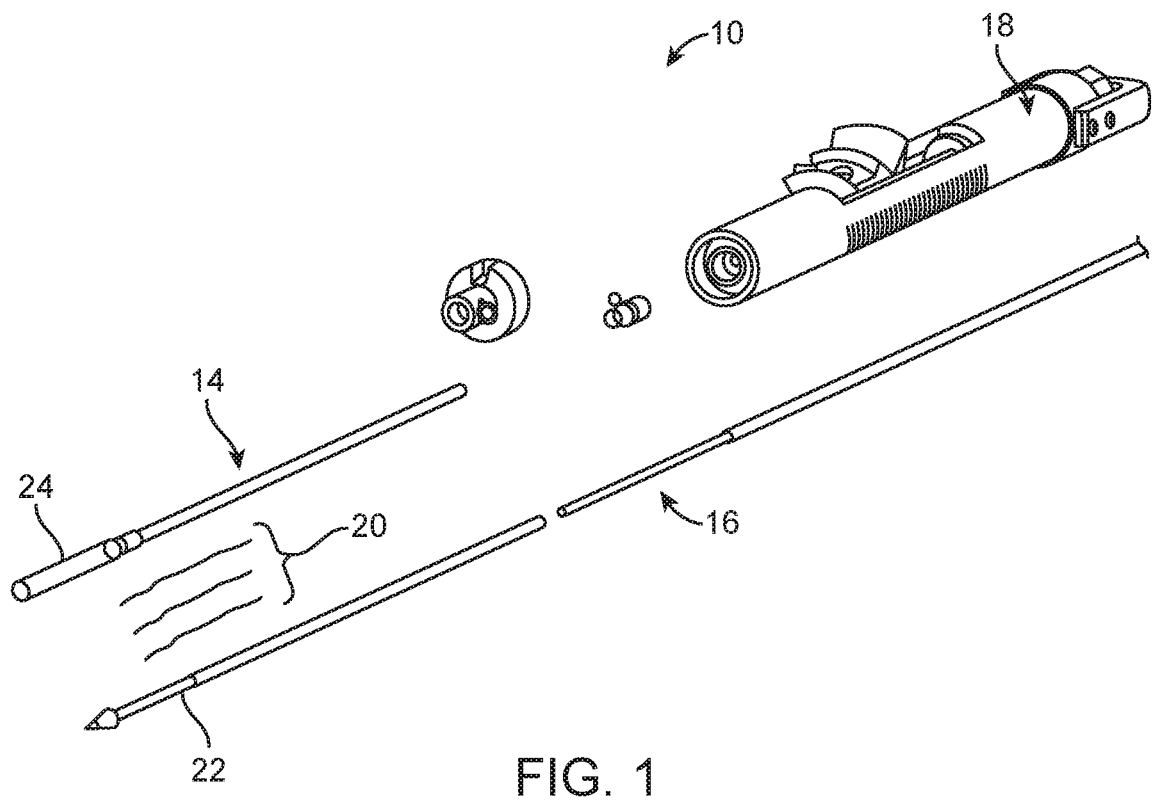
FIG. 1 is a perspective view of a delivery device for delivering a stented prosthetic heart valve or other stented prosthesis.
Figure 2A:
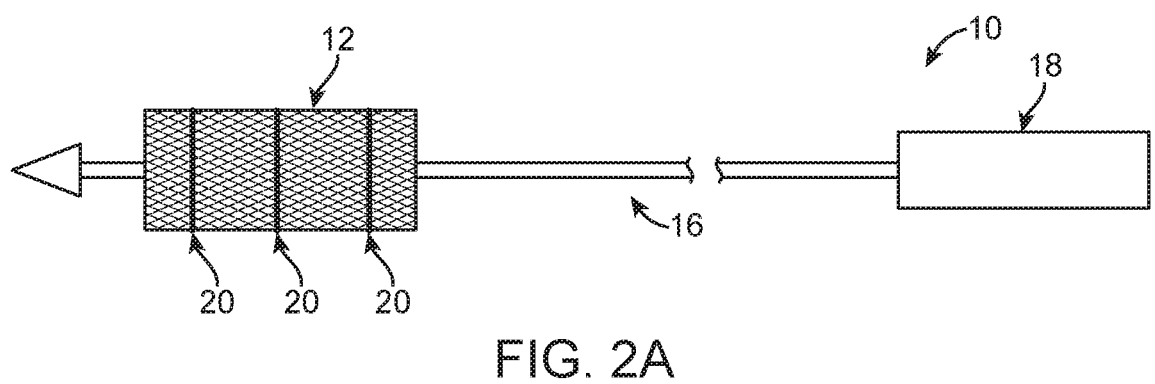
FIG. 2A is a partial, schematic illustration of the delivery device of FIG. 1 having the stented prosthetic heart valve positioned over an inner shaft assembly; the stented prosthetic heart valve shown in an expanded arrangement.
Figure 2B:
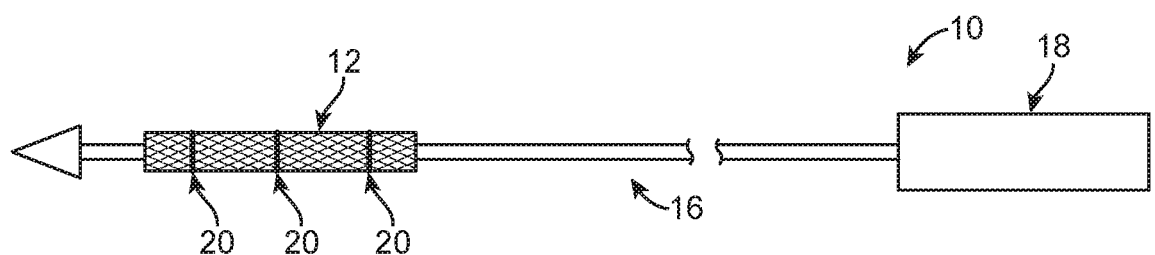
FIG. 2B is a schematic illustration of the delivery device of FIG. 2A having the stented prosthetic heart valve positioned over the inner shaft assembly with a plurality of tension members in a compressed arrangement.

As described below, some aspects of the present disclosure relate to transcatheter stented prosthetic heart valve delivery devices utilizing one or more elongate tension members to retain the stented prosthetic heart valve during delivery to a target site. It will be understood that the delivery devices can also be used to deliver other stented prostheses as well in a similar manner. By way of background, general components of one non-limiting example of a delivery device 10 with which some embodiments of the present disclosure are useful are illustrated in FIGS. 1-2B. The delivery device 10 is arranged and configured for percutaneously delivering a stented prosthetic heart valve 12 (hereinafter "prosthetic valve") to a patient's native defective heart valve. The delivery device 10 includes an optional outer sheath assembly 14, an inner shaft assembly 16 and a handle assembly 18. One or more elongate tension members 20 (e.g., sutures, chords, wires or filaments) are provided, and can be considered part of the delivery device 10 in some embodiments or as part of the prosthetic valve 12 or stented prosthesis in other embodiments. The delivery device 10 provides a loaded, compressed arrangement (FIG. 2B) in which the prosthetic valve 12 is loaded over the inner shaft assembly 16 and is compressively retained on a distal portion 22 by the tension members 20. As is schematically illustrated in FIGS. 2A-2B, compression of the prosthetic valve 12 is adjustable with the one or more tension members 20. Once loaded and compressed, the prosthetic valve 12 is located at a target site, tension in the tension members 20 is lessened or released to permit the prosthetic valve 12 to self-expand to an expanded arrangement, partially releasing and ultimately fully deploying the prosthetic valve 12 from the inner shaft assembly 16 (see, FIG. 2A). In this embodiment, the outer sheath assembly 14 includes a capsule 24 that is selectively disposed over the prosthetic valve 12 that assists in constraining the prosthetic valve 12 in the compressed arrangement and can be retracted by the handle assembly 18 to expose the prosthetic valve 12. The present disclosure focuses on numerous ways to incorporate at least one bumper into a delivery device, such as the delivery device 10.

As referred to herein, stented prostheses, stented prosthetic heart valves or "prosthetic valves" useful with the various devices and methods of the present disclosure may assume a wide variety of configurations. Stented prosthetic heart valves can include, for example, a bioprosthetic heart valve having tissue leaflets or a synthetic heart valve having polymeric, metallic or tissue-engineered leaflets, and can be specifically configured for replacing valves of the human heart. The prosthetic valves and stented prostheses of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

One non-limiting example of a stented prosthesis, that being a stented prosthetic heart valve 30, is illustrated in FIGS. 3A-3B. As a point of reference, the prosthetic valve 30 is shown in a normal or expanded arrangement in the view of FIG. 3A and a compressed arrangement in FIG. 3B. The prosthetic valve 30 includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the prosthetic valve 30 can be achieved with one or more tension members 20.

If provided, the valve structure 34 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 3A-3B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The prosthetic valve 30 includes a first end 40 and an opposing second end 44 of the prosthetic valve 30. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around frame 32 (only one post 46 is visible in FIG. 3A).

Figure 4C:
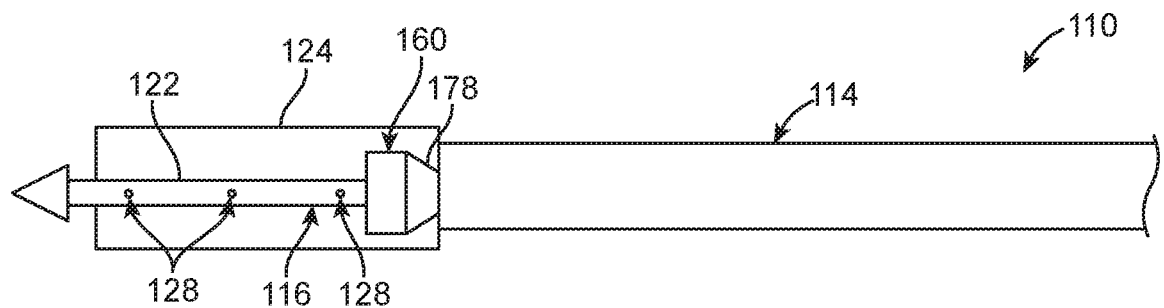
FIG. 4C is a partial, schematic illustration of the delivery device of FIGS. 4A-4B; wherein the capsule is advanced over the bumper and the compressed stented prosthetic heart valve.
Figure 4D:
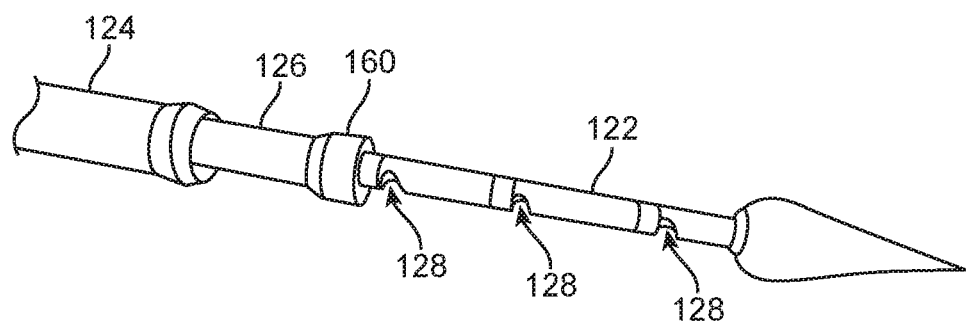
FIG. 4D is a perspective view of the delivery device of FIGS. 4A-4C.

FIGS. 4A-4F illustrate portions of a delivery device 110 that is largely similar to that of FIGS. 1-2B. FIGS. 4A-4D show the delivery device 110 prior to having the prosthetic valve 30 of FIGS. 3A-3B or other stented prosthesis loaded thereto. The delivery device 110 includes an outer sheath assembly 114, an inner shaft assembly 116, and can further include a handle assembly (such as handle assembly 18 of FIG. 1). The delivery device 110 is configured to translate between two states for positioning a capsule 124 of the outer sheath assembly 114 (the capsule 124 is shown in FIG. 4C as transparent for ease of illustration). The capsule 124 covers the prosthetic valve 30 during delivery so that the stent frame 32 does not scrape the patient's anatomy. In the state of FIG. 4A, the capsule 124 is retracted with respect to the inner shaft assembly 116. In the state of FIG. 4C, the capsule 124 is advanced over a distal portion 122 of the inner shaft assembly 116. As seen in FIG. 4D, the distal portion 122 includes a plurality of prosthesis retaining features 128, such as apertures, for receiving at least one tension member as will be discussed in further detail below.

The delivery device 110 also includes a bumper 160 defining a cavity 180 that is threaded over the inner shaft assembly 116. The bumper 160 is optionally secured to a middle tube 126 that is longitudinally fixed with respect to the inner shaft assembly 116. The bumper 160 is positioned adjacent the most proximal aperture 128 so that when the prosthetic valve 30 is secured on the distal portion 122 and the outer sheath assembly 114 is retracted as is shown in FIG. 4A, the bumper 160 is distal the capsule 124. The bumper 160 is also configured to have a ramped surface 178 that provides a smooth transition as the capsule 124 is advanced over the compressed prosthetic valve 30 as will be further discussed below. Although shown as a unitary structure, the bumper 160 can be constructed of a plurality of pieces in alternate embodiments.

FIG. 4B illustrates various proportions of the delivery device 110. For example, the illustrated bumper 160 has a tapered outer diameter at least partially defined by a distal outer diameter DD at a distal end 162 and a proximal outer diameter PD at a proximal end 164 and the ramped surface 178, which is located between the distal and proximal ends 162, 164. When the prosthetic valve 30 is in the fully compressed arrangement on the distal portion 122 and retained thereto with one or more tension members 20, the proximal outer diameter PD is greater than or equal to an outer diameter VD of the prosthetic valve 30 (see also, FIG. 3B and FIG. 4E). The distal outer diameter DD of the bumper 160 is greater than that of the ramped surface 178 and the proximal outer diameter PD of the bumper 160. Although exaggerated in the schematic views of FIGS. 4A-4C and 4E-4F for ease of understanding, in actual practice, the distal outer diameter DD of the bumper 160 is only slightly less than an inner diameter ID of the capsule 124 as is depicted in FIG. 4D.

Figure 4E:
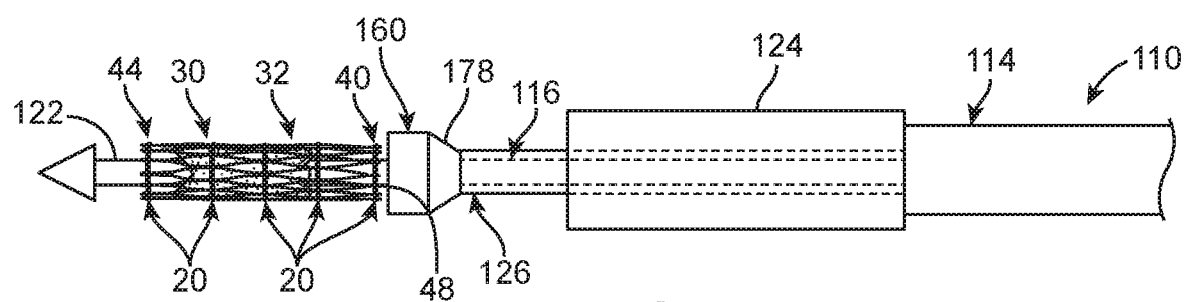
FIG. 4E is a partial, perspective view of the delivery device of FIGS. 4A having the compressed stented prosthetic heart valve of FIG. 3B loaded thereto.

FIG. 4E illustrates the delivery device 110 having the prosthetic valve of FIGS. 3A-3B loaded thereto. In this view, the outer sheath assembly 114 is retracted so that the prosthetic valve 30 can be compressively retained on the distal portion 122 with the tension member(s) 20. The tension members 20 are threaded around the stent frame 32 and then through one of the plurality of valve retaining features 128 to a handle assembly (such as handle assembly 18) or other mechanism for controlling and releasing the one or more tension members 20. As in the embodiment of FIGS. 1-2B, compression of the prosthetic valve 30 is adjustable with the one or more tension members 20.

Figure 4F:
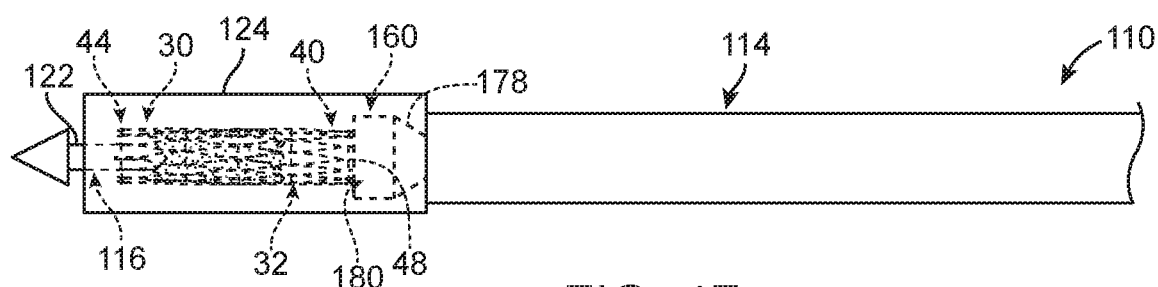
FIG. 4F is a partial, perspective view of the delivery device of FIGS. 4A-4E when the capsule is advanced over the bumper and the stented prosthetic heart valve.

Once the prosthetic valve 30 is loaded onto the distal portion 122 adjacent the bumper 160, the capsule 124 of the outer sheath assembly 114 is positioned over the prosthetic valve 30 as is shown in FIG. 4F. As discussed above, the bumper 160 provides the ramped surface 178 for easing the movement of the capsule 124 over the prosthetic valve 30. At this stage, the prosthetic valve 30 is sheathed and ready for delivery. Once the prosthetic valve 30 is delivered and ready to be deployed at a target site, the outer sheath assembly 114 is retracted to unsheathe the prosthetic valve 30. As the outer sheath assembly 114 is retracted, the bumper 160 provides support and the ramped surface 178 for the capsule 124 to travel across. After the capsule 124 is retracted, tension in each tension member 20 is lessened or released to permit the prosthetic valve 30 to self-expand, partially releasing and ultimately fully deploying the prosthetic valve 30 from the distal portion 122. Next, each tension member 20 is released from the prosthetic valve 30 and withdrawn from the patient along with the delivery device 110.

Figure 5A:
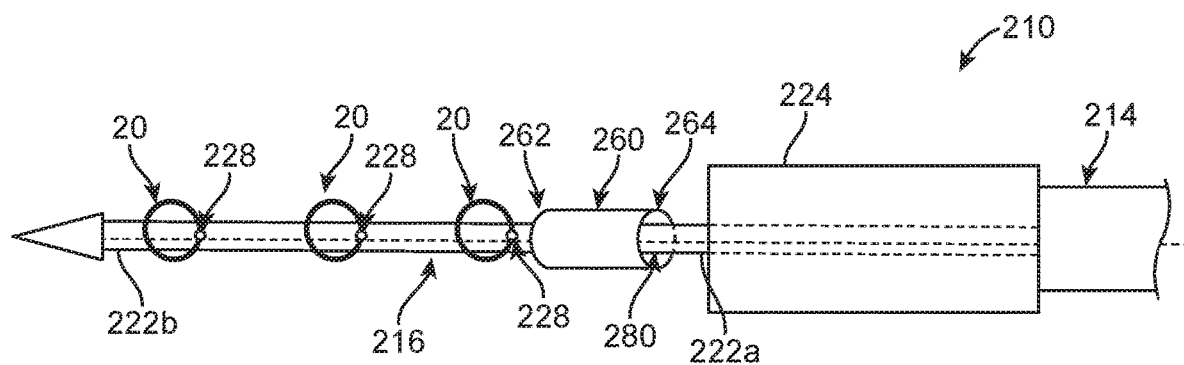
FIG. 5A is a partial, schematic illustration of a delivery device having a bumper that can provide smooth transition between a capsule and the stented prosthetic heart valve of FIG. 3 when in the compressed arrangement; wherein the bumper is also configured to connect a distal portion on which the stented prosthetic heart valve resides to a proximal shaft of an inner shaft assembly.
Figure 5B:
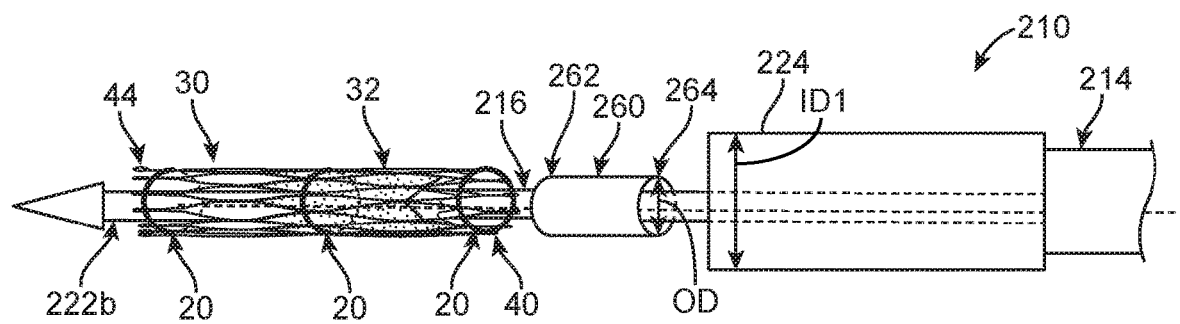
FIG. 5B is a partial, schematic illustration of the delivery device of FIGS. 5A-5B with the stented prosthetic valve of FIG. 3B loaded thereto.
Figure 5C:
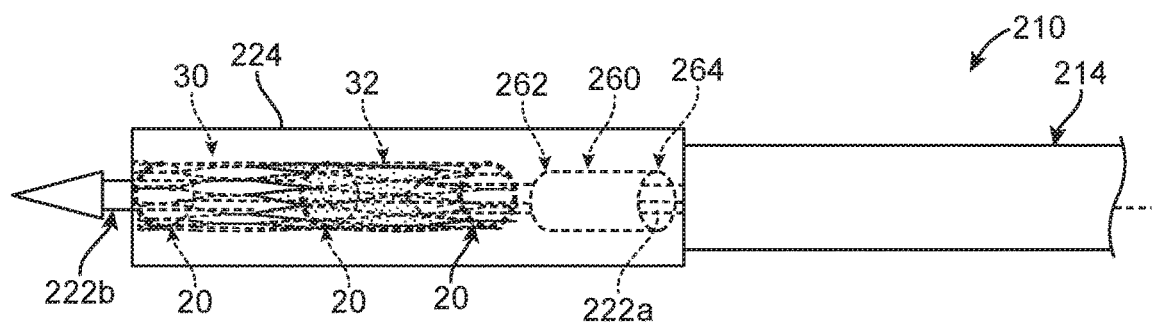
FIG. 5C is a partial, schematic illustration of the delivery device of FIG. 5A when the capsule is advanced over the stented prosthetic heart valve.

The delivery device 210 of FIGS. 5A-5C is largely similar to the delivery device 110 of FIGS. 4A-4F, except that the bumper 160 is replaced with an alternate bumper 260 that is configured to not only provide a smooth transition as a capsule 224 of an outer shaft assembly 214 is advanced over the compressed prosthetic valve 30 or other stented prosthesis but also to connect various elements of an inner shaft assembly 216. FIG. 5A illustrates the delivery device 210 prior to loading of the prosthetic valve 30. In this embodiment, the inner shaft assembly 216 has a proximal shaft 222a and a distal shaft or distal portion 222b. The proximal shaft 222a and the distal portion 222b can be coupled and de-coupled with the bumper 260 at a cavity 280 defined by the bumper 260. The bumper 260 can include elements or features (not shown) that engage respective elements of the proximal shaft 222a and/or the distal portion 222b. The bumper 260 can be fixedly secured to one of the proximal shaft 222a or the distal portion 222b or can be capable of coupling and de-coupling the proximal shaft 222a to the distal portion 222b. The distal portion 222b also includes a plurality of valve retaining features 228, such as apertures, each for receiving at least one tension member 20 for adjustably compressing the prosthetic valve 30. Although not illustrated, the bumper 260 can optionally include a ramped surface and a proximal end 264 having a smaller outer diameter as compared to an outer diameter of a distal end 262 of the bumper 260, as disclosed with respect to other embodiments (for example, see FIGS. 4B or 8A-8C and the related disclosure).

FIG. 5B illustrates the delivery device 210 having the prosthetic valve 30 of FIGS. 3A-3B loaded thereto. In this view, the capsule 224 is in a retracted position, proximal to the bumper 260 and the prosthetic valve 30. The bumper 260 is positioned adjacent the most proximal valve retaining feature 228 and distal to the capsule 224 when the capsule 224 is in the retracted position of FIG. 5B. FIG. 5C illustrates the outer shaft assembly 214 having been advanced to sheathe the prosthetic valve 30. As the capsule 224 moves from the position of FIG. 5B to the position of FIG. 5C, the bumper 260 provides a smooth transition surface to prevent the capsule 224 from snagging on any features 48 at the first end 40 of the prosthetic valve 30 or other stented prosthesis. In this embodiment, the bumper 260 has an outer diameter OD greater than the diameter VD of the compressed prosthetic valve 30, but less than an inner diameter ID1 of the capsule 224.

Figure 6A:
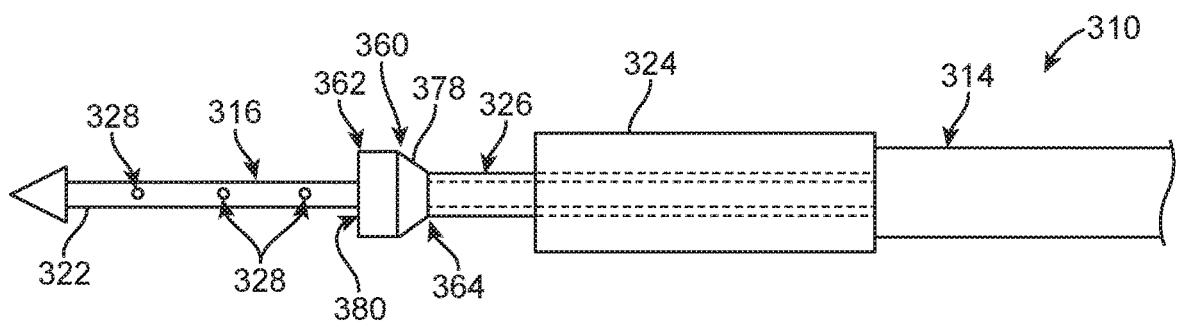
FIG. 6A is a partial, schematic illustration of an alternate delivery device having a bumper.

FIGS. 6A-6H illustrate yet another delivery device 310 similar to that of FIGS. 4A-4F except as explicitly stated. FIG. 6A illustrates the delivery device 310 prior to loading the prosthetic valve 30 or other stented prosthesis. The delivery device 310 includes an outer sheath assembly 314, an inner shaft assembly 316, and can include a handle assembly (not shown; see the handle assembly 18 of FIG. 1, for example). The inner shaft assembly 316 includes a distal portion 322 over which the prosthetic valve 30 of FIGS. 3A-3B can be secured with one or more tension members 20 (see FIGS. 6E-6H). The tension members 20 are positioned around the stent frame 32 and then through one of a plurality of prosthesis retaining features 328, such as apertures, to a handle assembly (e.g., the handle assembly 18 or other mechanism for controlling and releasing each tension member 20). The outer sheath assembly 314 includes a capsule 324 that can be selectively transitioned from a retracted position of FIG. 6A to an advanced position of FIG. 6D. As in prior disclosed embodiments, the capsule 324 and outer sheath assembly 314 can be retracted by the handle assembly (such as the handle assembly 18 of FIG. 1, for example) to expose the prosthetic valve 30.

The delivery device 310 further includes a bumper 360 defining a cavity 380 threaded over the inner shaft assembly 316. The bumper 360 is secured to an optional middle tube 326. In either configuration, the bumper 360 includes a ramped surface 378 that ensures a smooth transition as the capsule 324 advances over the bumper 360 and over the prosthetic valve 30. As seen in FIG. 6C, in this embodiment, the middle tube 326 is slidably secured over the inner shaft assembly 316 and within the outer sheath assembly 314 so that a longitudinal position of the bumper 360 is adjustable along the inner shaft assembly 316 to engage or at least partially cover the proximal end 40 of the prosthetic valve 30. For example, the bumper 360 can be moved from the position of FIG. 6A to the positon of FIG. 6B.

Figure 6B:
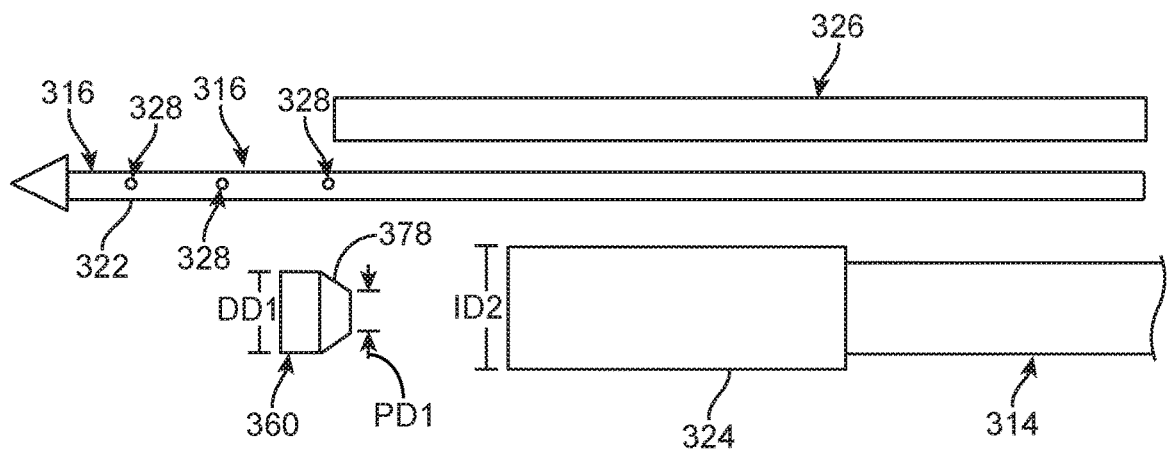
FIG. 6B is a partial, exploded, schematic illustration of the delivery device of FIG. 6A.
Figure 6C:
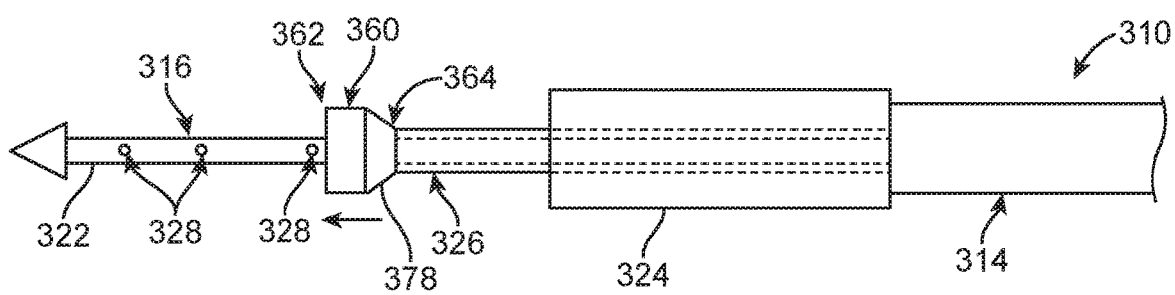
FIG. 6C is a partial, schematic illustration of the delivery device of FIGS. 6A-6B in which a middle tube is advanced distally as compared to FIG. 6A.
Figure 6D:
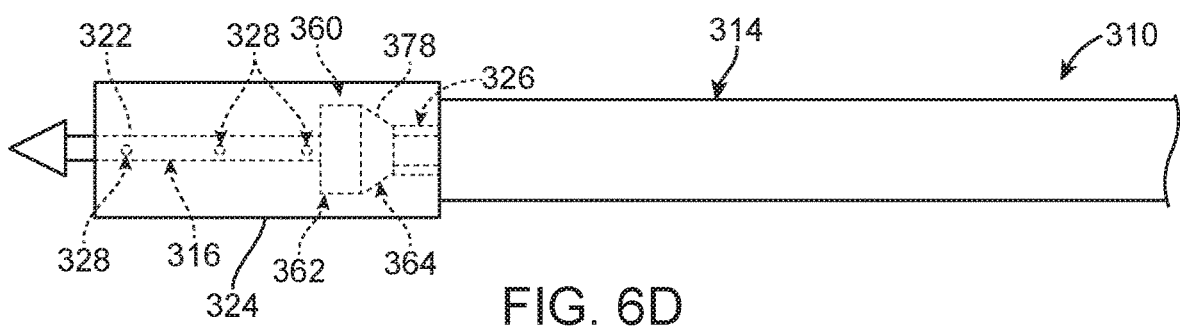
FIG. 6D is a partial, schematic illustration of the delivery device of FIGS. 6A-6C in which an outer sheath assembly has advanced a capsule over the bumper.

Turning now also to FIG. 6B, which illustrates various proportions of the delivery device 310 as compared to one another. The illustrated bumper 360 has a tapered outer diameter at least partially defined by the ramped surface 378, a distal outer diameter DD1 at a distal end 362 and a proximal outer diameter PD1 at a proximal end 364. When the compressed prosthetic valve 30 of FIG. 3B or other stented prosthesis is secured over the distal portion 322, as illustrated in FIGS. 6E-6H, the proximal outer diameter PD1 is greater than or equal to the outer diameter VD of the prosthetic valve 30 (see also, FIG. 3B). The distal outer diameter DD1 of the bumper 360 is greater than that of the ramped surface 378 and the proximal outer diameter PD1 of the bumper 360. Although exaggerated in the schematic views of FIGS. 6A-6H for ease of illustration, in actual practice, the distal outer diameter DD1 of the bumper 360 is only slightly less than an inner diameter ID2 of the capsule 324.

Figure 6E:
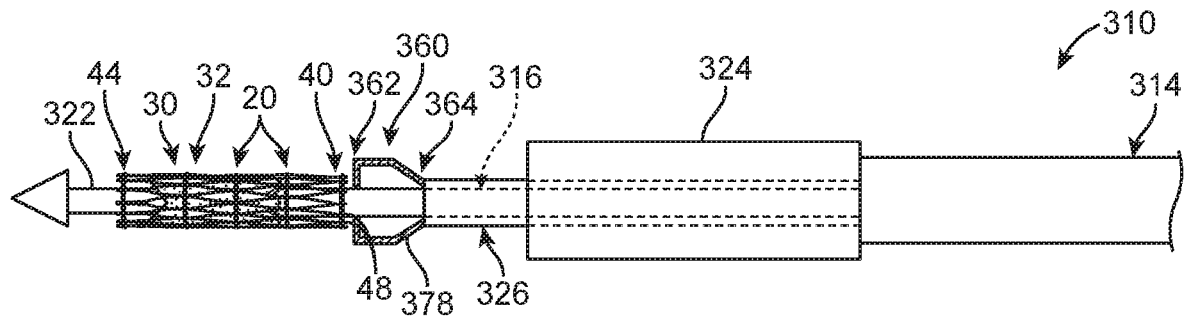
FIG. 6E is a partial, schematic illustration of the delivery device of FIGS. 6A-6D having the compressed stented prosthetic heart valve of FIG. 3B loaded thereto.
Figure 6F:
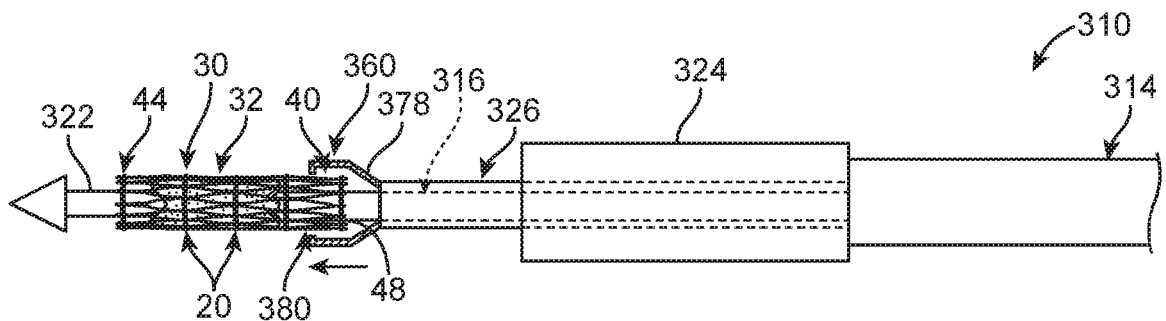
FIG. 6F is a partial, schematic illustration of the delivery device of FIGS. 6A-6E in a second loading position illustrating the bumper advanced distally with the middle tube over a proximal end of the stented prosthetic heart valve.
Figure 6G:
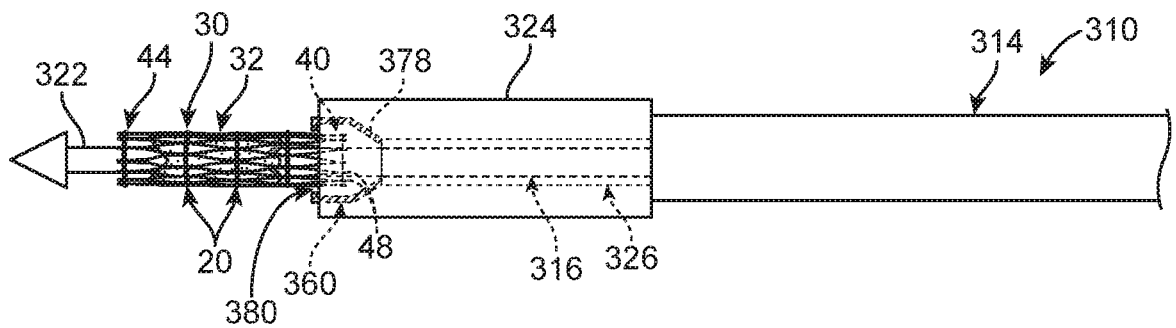
FIG. 6G is a partial, schematic illustration of the delivery device of FIGS. 6A-6F in a third loading position illustrating the capsule advanced distally over the bumper.

FIG. 6E illustrates the delivery device 310 in which the prosthetic valve 30 is loaded over the inner shaft assembly 316 and is compressively retained on a distal portion 322 by one or more tension members 20. As in the embodiments disclosed above, the prosthetic valve 30 is adjustably compressed with the one or more tension members 20. At this first loading step, the capsule 324 and bumper 360 are proximal to the prosthetic valve 30. To continue loading the prosthetic valve 30, as shown in FIG. 6F, the middle tube 326 is advanced distally over the inner shaft assembly 316 until the bumper 360 engages or covers at least part of the proximal, first end 40 of the prosthetic valve 30. Once the first end 40 is at least partially covered by the bumper 360, any features 48 located at the first end 40 of the prosthetic valve 30 are encased by the bumper 360 so that when the capsule 324 is advanced to the position of FIG. 6G, the capsule 324 travels over the smooth, ramped surface 378 and over the stent frame 32 to the position of FIG. 6H without snagging on any of the features 48.

Figure 6H:
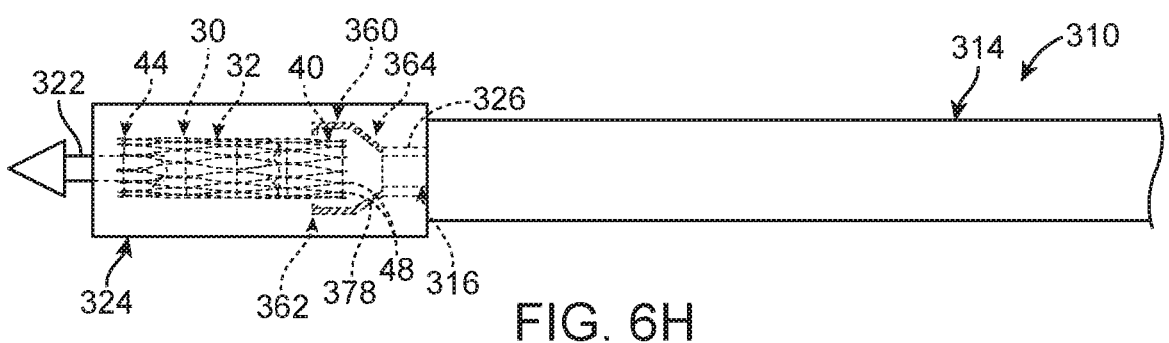
FIG. 6H is a partial, schematic illustration of the delivery device of FIGS. 6A-6G in a fourth loading position illustrating the capsule advanced further over the stented prosthetic heart valve.

FIG. 6H illustrates the delivery device 310 in which the fully loaded prosthetic valve 30 is sheathed by the capsule 324. Once the loaded and compressed prosthetic valve 30 is located at a target site, the bumper 360 is retracted and then the capsule 324 is retracted back to the position of FIG. 6E. Next, tension in each tension member 20 is lessened or released with a handle assembly (such as handle assembly 18 of FIG. 1) to permit the prosthetic valve 30 to self-expand, partially releasing and ultimately fully deploying the prosthetic valve 30 from the distal portion 322. Then, the tension member(s) 20 are released from the prosthetic valve 30 and withdrawn from patient along with the delivery device 310.

Figure 7A:
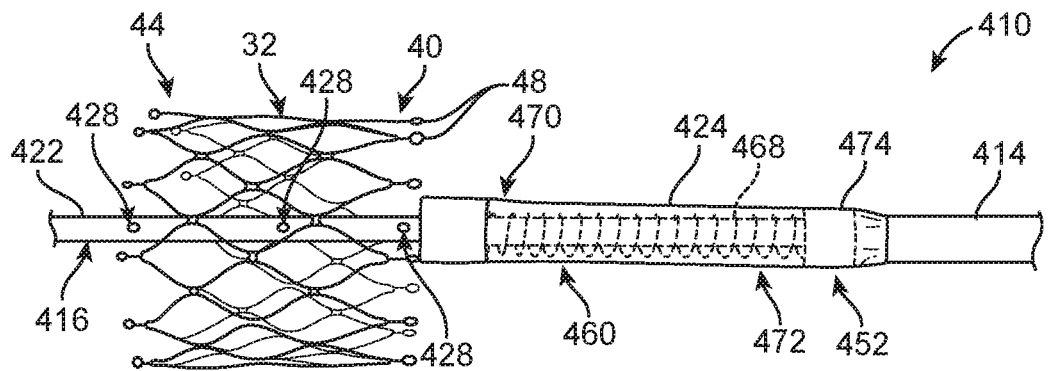
FIG. 7A is a partial, side view of an alternate delivery device for delivering the stented prosthetic heart valve of FIGS. 3A-3B (only a stent frame of the stented prosthetic heart valve is shown for clarity).
Figure 7B:
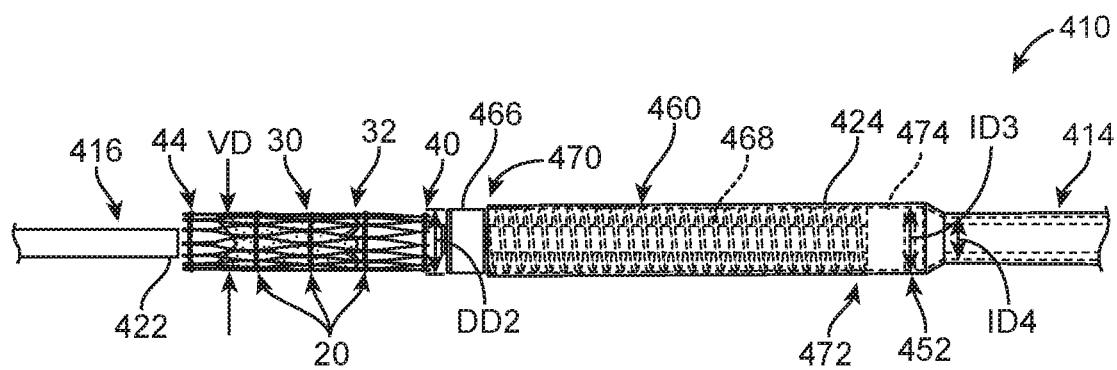
FIG. 7B is a partial, side view of the delivery device of FIG. 7A, the delivery device including a bumper assembly having a distal bumper, a proximal bumper and a biasing member secured therebetween.
Figure 7C:
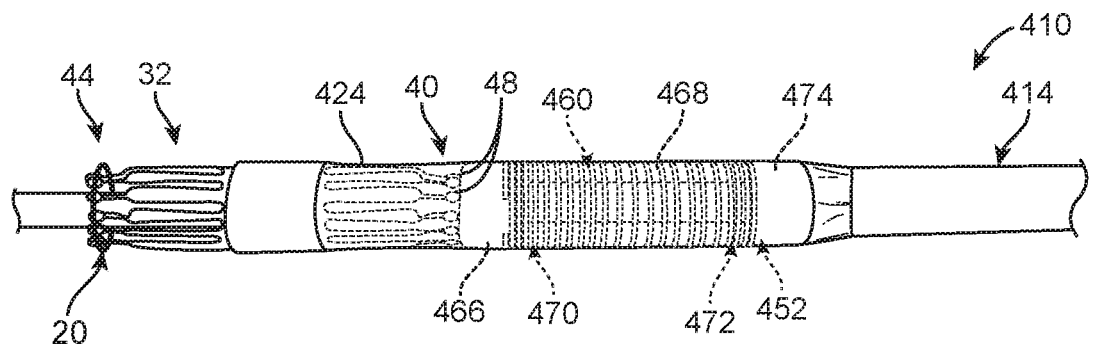
FIG. 7C is a partial, side view of the delivery device of FIGS. 7A-7B, the capsule advanced distally to cover the stented prosthetic heart valve and the biasing member compressing to accommodate distal translation of the capsule over the stent frame.
Figure 7D:
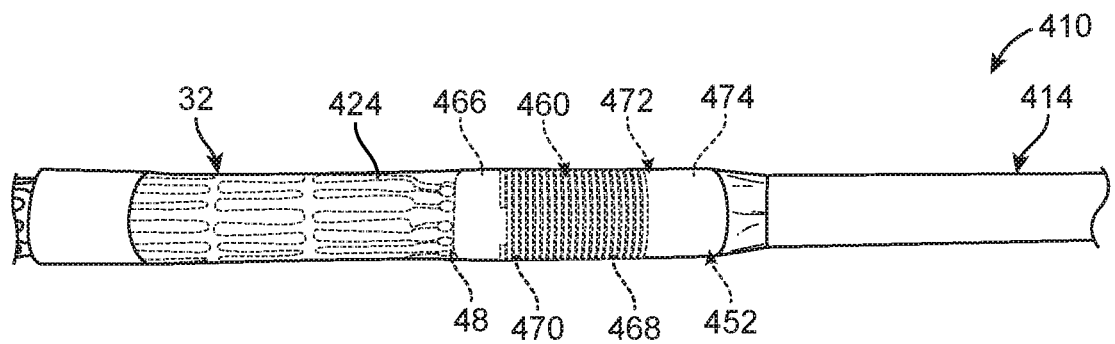
FIG. 7D is a partial, side view of the delivery device of FIGS. 7A-7C, the capsule further advanced to cover the stent frame and the biasing member further compressing to accommodate the stent frame received loaded within the capsule.

FIGS. 7A-7D illustrate an alternate delivery device 410 arranged and configured for percutaneously delivering the prosthetic valve 30 or other stented prosthesis to a target site (in FIGS. 7A and 7C-7D, only the stent frame 32 of the prosthetic valve 30 of FIGS. 3A-3B is shown for clarity). The delivery device 410 can be configured similar to the delivery device 10 of FIGS. 1-2B except as explicitly stated. The delivery device 410 includes an outer sheath assembly 414, an inner shaft assembly 416, and can further include a handle assembly (not shown; see handle assembly 18 of FIG. 1, for example). The delivery device 410 provides a loaded delivery state in which the stent frame 32 is loaded over and is compressively retained on a distal portion 422 of the inner shaft assembly 416 with one or more tension members 20. The tension members 20 are each wrapped around the stent frame 32 and then threaded through valve retaining features 428 (e.g., apertures) in the distal portion 422 to an actuating mechanism (such as the handle 18 of FIG. 1) for adjusting the tension and ultimately releasing the tension members 20 from the prosthetic valve 30.

The delivery device 410 also includes a bumper assembly 460 having a distal bumper 466 secured to a distal end 470 of a biasing member 468 positioned within the capsule 424 and a proximal bumper 474 secured to a proximal end 472 of the biasing member 468. The distal bumper 466 is fixed to the inner shaft assembly 416 and the proximal bumper 464 is configured to slide along a length of the inner shaft assembly 416, within the capsule 424. Alternatively, the proximal bumper 464 is fixed to the inner shaft assembly 416 and the distal bumper 466 can translate freely within the capsule 424 during loading and recapture of the stent frame 32. As can be seen in FIG. 7B, an inner diameter ID3 of the capsule 424 is at least slightly greater than an inner diameter ID4 of the outer delivery sheath 414 immediately proximate the capsule 424 to retain the proximal bumper 474 within the capsule 424 as the capsule 424 is advanced and the biasing member 468 pushes the proximal bumper 474 proximally in response to the force applied by loading the prosthetic valve 30 within the capsule 424. In example embodiments, the biasing member 468 is a coil spring made of metal or polymeric material.

The bumper assembly 460 is provided, in part, to provide a smooth transition and ease loading of the stent frame 32 within the capsule 424. As discussed above with respect to prior embodiments, various features 48 at the end 40 of the stent frame 32 can catch on the capsule 424 during sheathing of the prosthetic valve 30 within the capsule 424. The bumper assembly 460 provides a distal bumper 466 having an outer diameter DD3 that is slightly less than an inner diameter of the capsule ID3 but greater than the outer diameter VD of the compressed prosthetic valve 30.

The bumper assembly 460 is also configured to deflect the capsule 424 away from the inner shaft assembly 416 of the delivery device 410 and to provide kink resistance to the capsule 424. As the capsule 424 is retracted proximally to expose the stent frame 32, the biasing member 468 expands to fill a volume of the capsule 424 that would otherwise be open between the stent frame 32 and a proximal end 452 of the capsule 424. The bumper assembly 460 is beneficial in that it increases the strength of the capsule 424 without increasing the profile of the capsule 424 during delivery.

As shown in FIG. 7A, the first step of loading the prosthetic valve 30 is positioning the naturally expanded stent frame 32 over the inner shaft assembly 416. At this stage, the proximal bumper 464 and biasing member 468 of the bumper assembly 460 are positioned within the capsule 424 and the distal bumper 466 is positioned between the capsule 424 and the stent frame 32. Then, the stent frame 32 is compressed onto the distal portion 422 with the tension members 20 as shown in FIG. 7B either by actuating a handle assembly, for example handle assembly 18 of FIG. 1 or otherwise tensioning the tension members 20.

Once the prosthetic valve 30 is compressed, the outer sheath assembly 414 is advanced distally over the distal bumper 466 and over the prosthetic valve 30 as is generally illustrated in FIG. 7C. As with prior disclosed bumpers, the distal bumper 466 is configured to provide for a smooth transition as the capsule 424 advances over the proximal, first end 40 of the stent frame 32. The outer diameter DD3 of the distal bumper 466 is slightly less than that of the inner diameter ID3 of the capsule 424 but is larger than the diameter VD of the compressed prosthetic valve 30. In this view, the tension members 20 of FIG. 7B that are used to compress the prosthetic valve 30 are omitted so the prosthetic valve 30 has partially expanded. The prosthetic valve 30 is compressed until compression in the tension members 20 is released for deploying the prosthetic valve 30. As the capsule 424 is advanced distally, either during loading of the stent frame 32 into the capsule 424 or to recapture the stent frame 32 within the capsule 424, the biasing member 468 is forced to compress and provide space for the capsule 424 to sheathe the stent frame 32. Therefore, the biasing member 468 is selected to be weak enough as to not significantly affect loading and recapture forces and ability.

To fully load and sheathe the prosthetic valve 30, the outer sheath assembly 414 is further advanced distally until the prosthetic valve 30 is entirely sheathed by the capsule 424 as is seen in FIG. 7D. At this time, the biasing member 468 is in its most compressed state to provide room within the capsule 424 for the stent frame 32. After the prosthetic valve 30 is fully sheathed, as seen in FIG. 7D, the prosthetic valve 30 is loaded and ready for delivery to a target site with the delivery device 410.

Figure 8A:
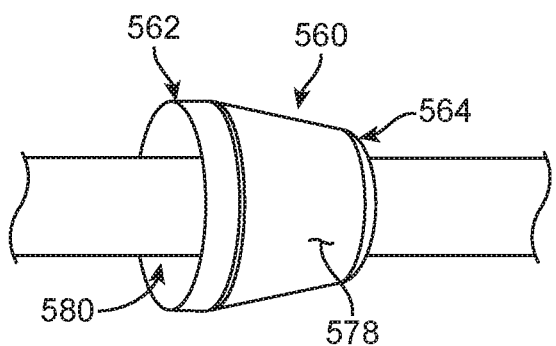
FIG. 8A is a perspective view of an alternate bumper that can be used with the delivery devices disclosed herein.
Figure 8B:
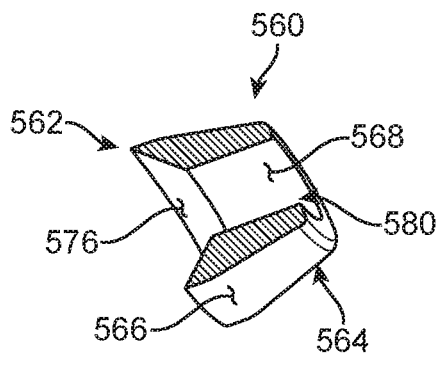
FIG. 8B is a cross-sectional view of the bumper of FIG. 8A.
Figure 8C:
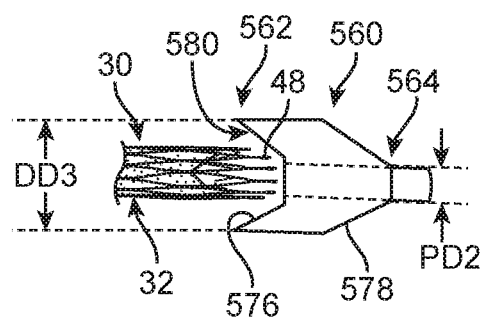
FIG. 8C is a schematic, cross-sectional view of the bumper of FIGS. 8A-8B.

FIGS. 8A-8C illustrate an alternate bumper 560 useful with the delivery devices 10, 110, 110', 210, 410 disclosed herein. The bumper 560 includes a distal end 562, a proximal end 564, an outer surface 566 and an inner surface 568. The outer surface 566 includes a ramped surface 578 formed by a tapered outer diameter such that a distal outer diameter DD3 is greater at the distal end 564 than a proximal outer diameter PD2 at the proximal end 564. The inner surface 568 defines a cavity 580 and is configured to have a tapered surface 576 at the distal end 562 within which the stent frame 32 can nest when the prosthetic valve 30 is in the compressed arrangement as shown in FIG. 8C.

Figure 9:
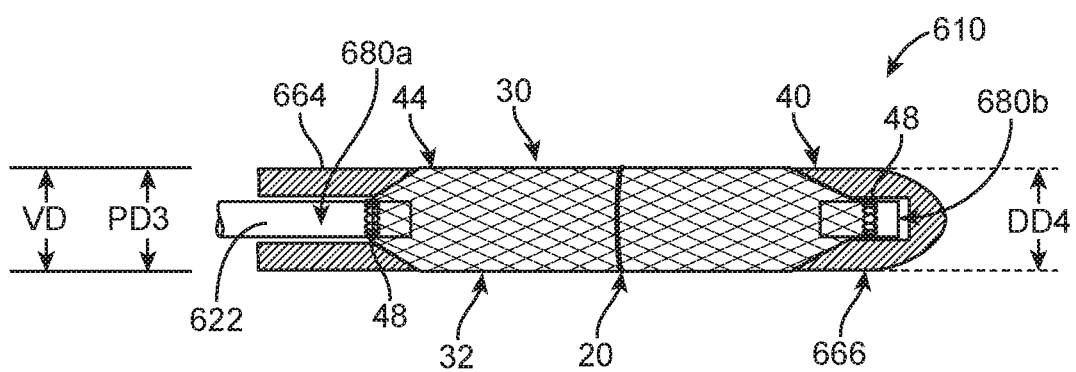
FIG. 9 is a partial, schematic illustration of an alternate delivery device having proximal and distal bumpers for delivery of the stented prosthetic heart valve of FIGS. 3A-3B.

By way of background, FIG. 9 generally illustrates the compressed prosthetic valve 30 of FIG. 3B loaded to an alternate delivery device 610 of which only certain components are shown. The delivery device 610 is can be similar to that described and illustrated with respect to FIGS. 1-2B except as otherwise stated. In this embodiment, the prosthetic valve 30 or other stented prosthesis is positioned on a distal portion 622 of the delivery device 610 by at least one tension member 20. The delivery device 610 includes proximal and distal bumpers 664, 666 assembled to and projecting radially from the distal portion 622. The bumpers 664, 666 are generally configured to selectively receive and cover a portion of a corresponding end 40, 44 of the prosthetic valve 30. For example, each of the bumpers 664, 666 define a cavity 680a, 680b that is sized to receive and maintain corresponding ends 40, 44 of the prosthetic valve 30 in its compressed arrangement of FIGS. 3B and 9. Further, a longitudinal spacing between the bumpers 664, 666 is selected in accordance with an expected length of the prosthetic valve 30 in the compressed arrangement. With this construction the prosthetic valve 30 is maintained in the compressed arrangement having its ends 40, 44 smoothed via the bumpers 664, 666 to prevent snagging and injury to the patient during the delivery procedure. Alternate embodiments include only the distal bumper 666 and rely on one or more proximally positioned tension members or the like (not shown in FIG. 9, see also FIG. 3B) to compress the opposing end 44 of the stent frame 32. For example, one tension member (not shown) can be threaded through eyelets 48 (see also, FIG. 3B) at the proximal, second end 44 of the stent frame 32.

When provided, each of the proximal and distal bumpers 664, 666 are arranged and configured to cover at least a portion of the respective first and second ends 40, 44, which may include rough or jagged features 48 (e.g., crowns and/or eyelets). In some embodiments, as shown in FIG. 9, an outer diameter PD3, DD4 of the proximal and/or distal bumpers 646, 666 are respectively equal to or less than the outer diameter VD of the compressed prosthetic valve 30 so that the profile of the loaded, compressed prosthetic valve 30 is not increased by the delivery device 610. The proximal and distal bumpers 646, 666 keep the prosthetic valve 30 in a stretched, compressed position during the delivery procedure and also reduce the possibility that the prosthetic valve 30 will damage the patient's anatomy or loosen plaque during the delivery procedure, particularly trans-septal delivery procedures.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthesis to a target site; the delivery device comprising:
   an inner shaft assembly having a proximal shaft interconnected to a distal shaft, the distal shaft including a distal portion configured to retain the stented prosthesis;
   a bumper connected to the inner shaft assembly so that the inner shaft assembly extends through a cavity defined by the bumper, the bumper having a distal end, a proximal end and an outer surface; wherein the bumper selectively engages one of the proximal shaft and the distal shaft to selectively couple the proximal shaft and the distal shaft in an end-to-end configuration; wherein the proximal end has a smaller outer diameter as compared to an outer diameter of the distal end of the bumper; and
   an outer sheath assembly slidably secured over at least part of the inner shaft assembly; the outer sheath assembly having a capsule configured to slide distally and proximally to selectively sheathe and unsheathe the bumper and the stented prosthesis.

2. The delivery device of claim 1, wherein the distal portion includes a plurality of valve retaining features and the bumper is positioned adjacent the most proximal valve retaining feature.

3. The delivery device of claim 1, wherein the bumper is constructed of a unitary piece of material.

4. The delivery device of claim 1, wherein the bumper can be disconnected from only one of the proximal shaft and the distal shaft.

5. The delivery device of claim 1, further comprising one or more elongate tension members that can releasably retain the stented prosthesis when the stented prosthesis is on the inner shaft assembly.

6. The delivery device of claim 1, wherein the bumper includes a ramped surface between the proximal end and the distal end.

7. The delivery device of claim 2, wherein the valve retaining features are apertures.

* * * * *